United States Patent [19]

Hagiwara

[11] 4,398,534

[45] Aug. 16, 1983

[54] ELECTRICAL SURGICAL KNIFE DEVICE

[75] Inventor: Toshihiko Hagiwara, Hino, Japan

[73] Assignee: Olympus Optical Co., Ltd., Tokyo, Japan

[21] Appl. No.: 210,282

[22] Filed: Nov. 25, 1980

[30] Foreign Application Priority Data

Dec. 4, 1979 [JP] Japan .............................. 54-157282

[51] Int. Cl.³ .............................................. A61B 17/39
[52] U.S. Cl. ........................... 128/303.14; 128/303.17
[58] Field of Search ...................... 128/303.13, 303.14, 128/303.17

[56] References Cited

U.S. PATENT DOCUMENTS 3,885,569  5/1975  Judson .............................. 128/303.14
4,092,986  6/1978  Schneideman .................. 128/303.14

*Primary Examiner*—Lee S. Cohen
*Attorney, Agent, or Firm*—Frishauf, Holtz, Goodman and Woodward

[57] ABSTRACT

An electrical surgical knife device stops supplying an incision current, a coagulation current or a blend current whenever at least two of selection switches are actuated at the same time, said selection switches being provided for selecting the incision current, the coagulation current and the blend current, respectively.

5 Claims, 4 Drawing Figures

ELECTRICAL SURGICAL KNIFE DEVICE

BACKGROUND OF THE INVENTION

This invention relates to an electric surgical knife device.

A prior art electric surgical knife device supplies an incision current for incising body tissues, a coagulation current for coagulating the blood at the area of the incision and a blend current, i.e. blend of incision and coagulation currents, for both incising body tissues and coagulating the blood at the area of the incision. The incision current, the coagulation current and the blend current are supplied independently of one another by actuating respectively provided switches. An operating physician may mistakenly actuate two of these switches or all these switches at the same time. If this happens, the device may fail to supply the desired current. For example, when the physician mistakenly actuates the incision current supply switch and the coagulation current supply switch at the same time though he intends to coagulate the blood, the incision current may be supplied. In this case, the body tissue is cut without a blood coagulation procedure which will result in an enormous bleeding.

It is an object of this invention to provide an electric surgical knife device which helps carry out electric surgery in a safe and sound manner, if erroneously operated.

SUMMARY OF THE INVENTION

In accomplishing this object there has been provided according to this invention an electric surgical knife device which supplies no current when at least two of an incision current supply switch, a coagulation current supply switch and a blend current supply switch are actuated mistakenly at the same time.

This invention can be more fully understood from the following detailed description when taken in conjunction with the accompanying drawings:

DETAILED DESCRIPTION

Figure 1:
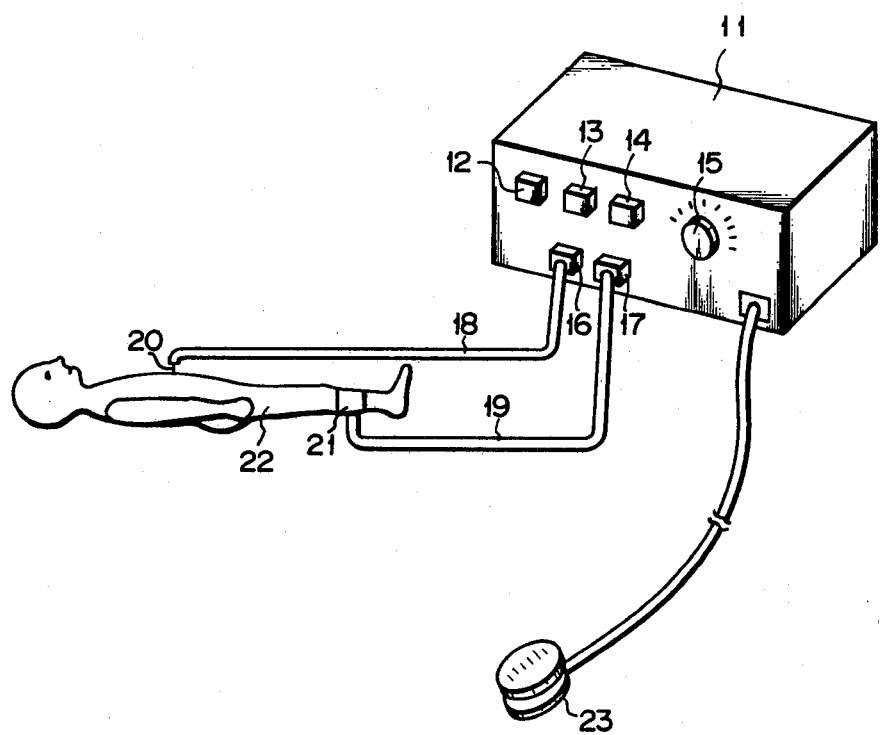
FIG. 1 is a perspective view of an electric surgical knife device according to this invention.

As shown in FIG. 1, an electric surgical knife device 11 according to this invention has three push button switches 12, 13 and 14. When actuated, the switches 12, 13 and 14 select an incision current, a coagulation current and a blend current, respectively. The device 11 is further provided with a knob 15 which is turned to adjust the level of the current selected. The device 11 further has two output terminals 16 and 17, to which two cords 18 and 19 are connected, respectively. The free end of the cord 18 is connected to an electric knife 20. The free end of the cord 19 is connected to a patient electrode 21 which is attached to a patient 22. To the electric surgical knife device 11 a foot switch 23 is connected.

Figure 2:
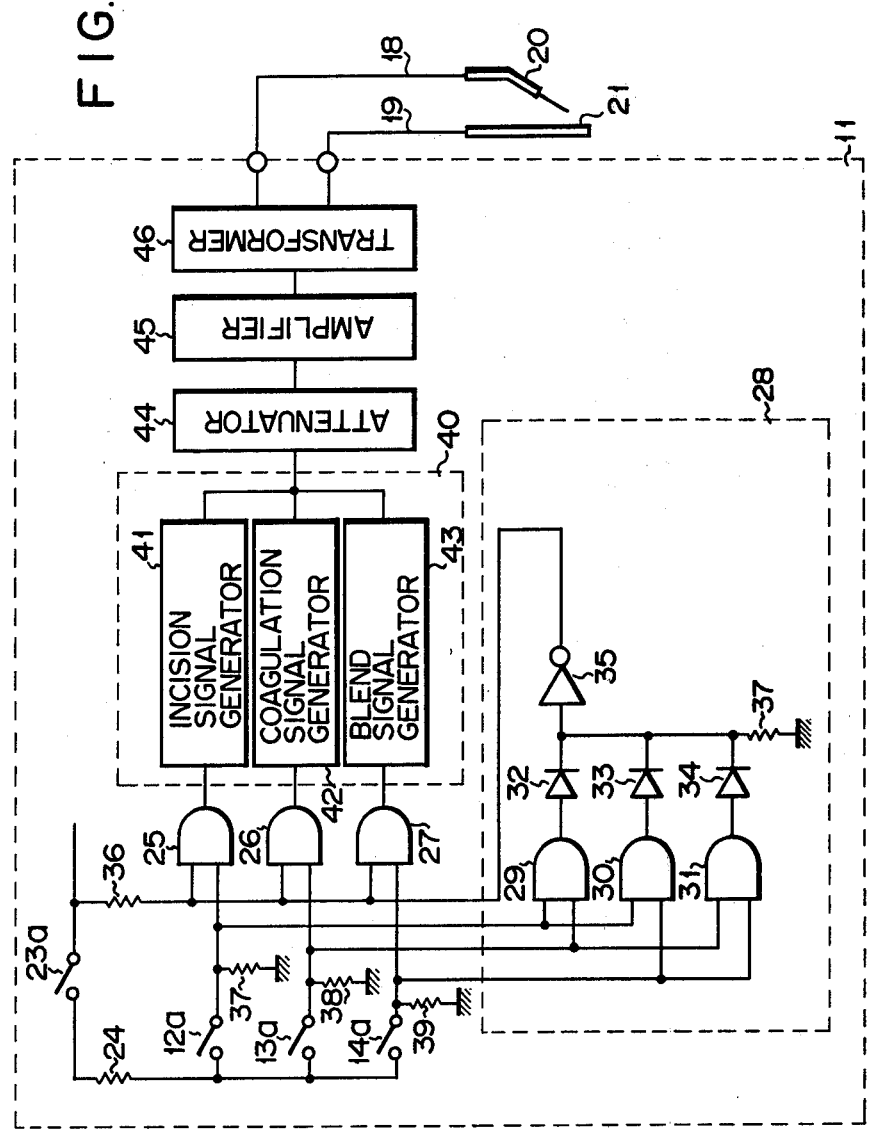
FIG. 2 is a circuit diagram of the electric surgical knife device shown in FIG. 1.

FIG. 2 shows the electrical circuit of the electric surgical knife device 11. As shown in FIG. 2, a power source of, for example, +5 V is connected through a foot switch 23a and a resistor 24 to one terminal of a selection switch 12a, one terminal of a selection switch 13a and one terminal of a selection switch 14a. The selection switches 12a, 13a and 14a are connected at the other terminal respectively to one input terminal of an AND gate 25, one input terminal of an AND gate 26 and one input terminal of an AND gate 27. The selection switches 12a and 13a are connected at the other terminal also to the two input terminals of an AND gate 29 of a detector circuit 28. The detector circuit 28 is so designed as to detect that two or three of the selection switches have been simultaneously actuated. The detector circuit 28 includes two other AND gates 30 and 31. The two input terminals of the AND gate 30 are connected respectively to the other terminal of the switch 12a and the other terminal of the selection switch 14a. The two input terminals of the AND gate 31 are connected respectively to the other terminal of the selection switch 13a and the other terminal of the selection switch 14a. The output terminals of the AND gates 29, 30 and 31 are connected to the input terminal of an inverter 35 respectively through a diode 32, a diode 33 and a diode 34. The output terminal of the inverter 35 is connected to the other input terminals of the AND gates 25, 26 and 27 and also to the +5 V power source via a resistor 36. The cathodes of the diodes 32, 33 and 34 are connected to the ground through a resistor 37.

The AND gates 25, 26 and 27 are connected at said one input terminal to the ground respectively through resistors 37, 38 and 39 which have a resistance higher than that of the resistor 24. The AND gates 25, 26 and 27 have their output terminals connected respectively to an incision signal generator 41, a coagulation signal generator 42 and a blend signal generator 43. The signal generators 41, 42 and 43 constitute a signal generating circuit 40. The signal generators 41, 42 and 43 are connected at the output terminal through an attenuator 44 to an amplifier 45. The output of the amplifier 45 is coupled to an output transformer 46. The output terminal of the transformer 46 is connected to the output terminals 16 and 17.

The electric surgical knife device having the above-described circuit is operated in the following manner.

Figure 3:
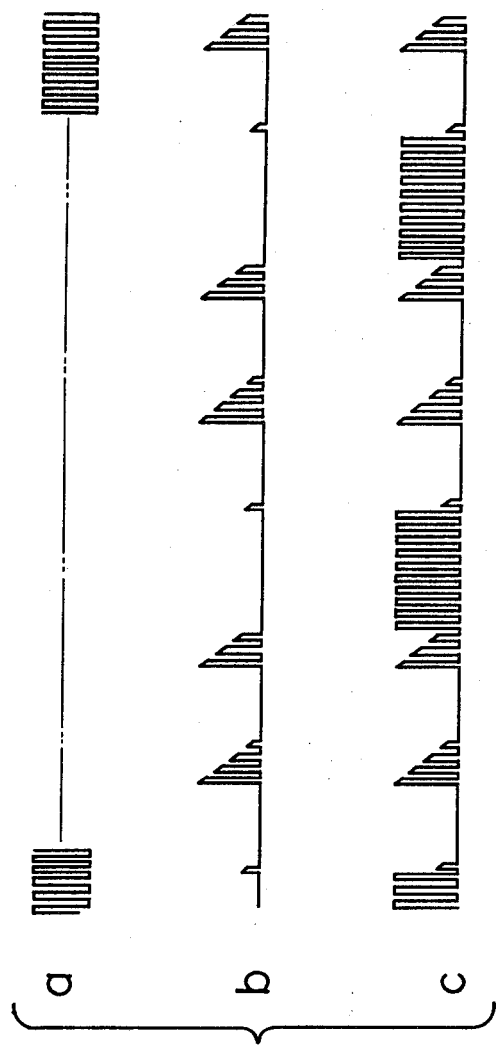
FIG. 3 shows the waveform of an incision current, the waveform of a coagulation current and the waveform of a blend current.

To supply an incision current, the button switch 12 is depressed, and the foot switch 23 is then pushed down. As a result, the selection switch 12a and the foot switch 23a are closed. Both input level of the AND gate 25 therefore go high, whereby the AND gate 25 produces an output signal of a high level. In response to the output signal of the AND gate 25 the incision signal generator 41 generates an incision signal a having such a waveform as illustrated in FIG. 3. The incision signal a is supplied to the amplifier 45 through the attenuator 44. The output signal of the amplifier 45, i.e. amplified incision signal a, is supplied to the output transformer 46, which supplies an incision current. The incision current thus obtained is applied between the electric knife 20 and the patient electrode 21 and thus flows through the patient 22 thereby to cut body tissues.

To supply a blend current, the button switch 14 is depressed. The button switch 12 is then released, and the selection switch 14b is closed. The blend signal generator 43 is therefore energized to generate a blend signal c having such a waveform as illustrated in FIG. 3. The blend signal c is converted into a blend current in the same way as the incision signal a is converted into an incision current. The blend current thus obtained is delivered from the output transformer 46.

To supply a coagulation current, the button switch 13 is depressed. Then, the coagulation signal generator 42 eventually generates a coagulation signal b, which is converted into a coagulation current in the same way as the incision signal and the blend signal are converted into an incision current and a blend current, respectively.

As mentioned above, it is possible with the electric surgical knife device of this invention to supply an incision current, a coagulation current or a blend current by actuating the button switch 12, 13 or 14.

It will now be described how the above-described electric surgical knife device operates if two or three button switches are erroneously depressed at the same time.

Suppose the operating physician pushes by mistake the button switches 12 and 13 at the same time, though he intends to apply a coagulation current on the patient. Then, the selection switches 12a and 13a are closed. If the foot switch 23a is closed under this condition, the AND gate 29 of the detector circuit 28 receives two input signals of a high level. The AND gate 29 therefore produces an output signal of a high level, which is supplied via the diode 32 to the inverter 35. The inverter 35 converts the input signal of a high level into a signal of a low level. The output signal of the inverter 35, which has a low level, is supplied to the other input terminals of the AND gates 25, 26 and 27. As a result, the output signals of the AND gates 25, 26 and 27 come to have a low level. None of the signal generators 41, 42 and 43 is actuated, and the electric surgical knife device 11 supplies no output current.

As mentioned above, the electric surgical knife device 11 supplies no output current if two button switches are depressed by mistake at the same time. Thus it is prevented that the body tissue not coagulated yet is cut, thus causing much bleeding.

Figure 4:
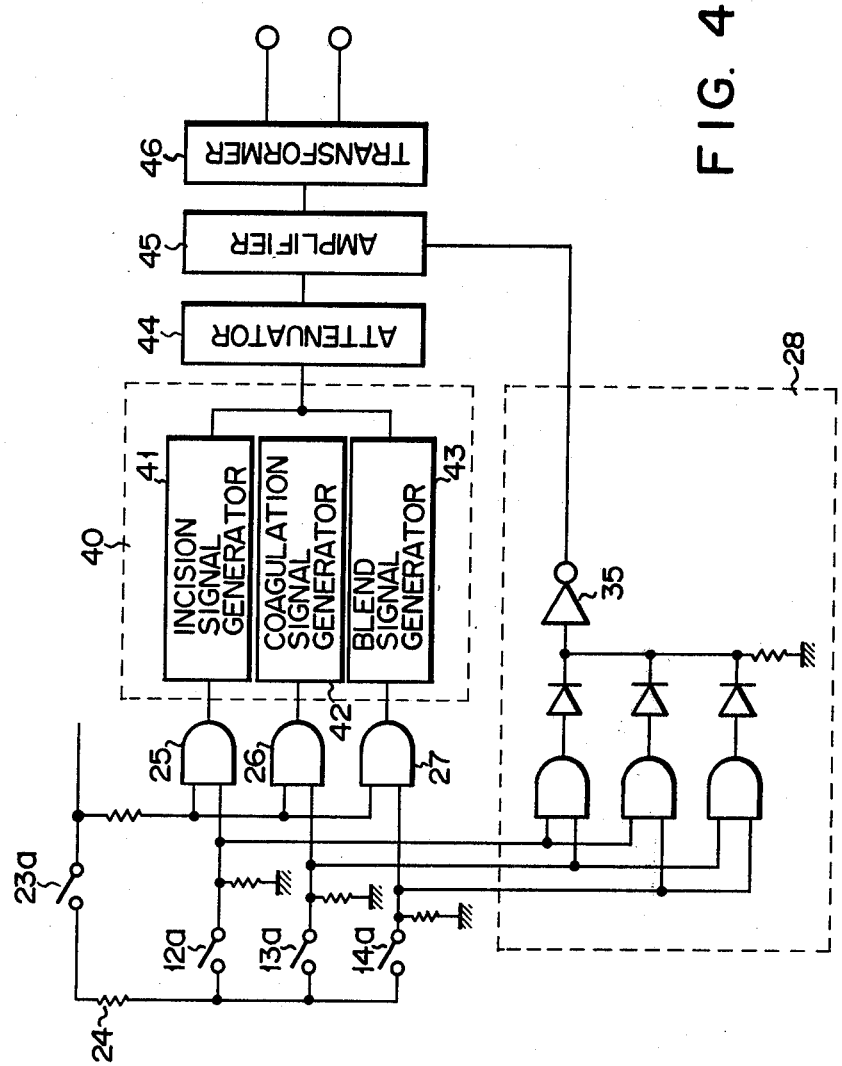
FIG. 4 is a circuit diagram of another electric surgical knife device according to this invention.

The electric circuit according to this invention is not limited to the circuit shown in FIG. 2 wherein the signal generating circuit 40 generates no output signal if two or three button switches are erroneously depressed at the same time. Instead, use may be made of such a circuit as shown in FIG. 4, wherein the output of a detector circuit 28, i.e. the output of an inverter 35, is supplied to an amplifier 45, thus preventing the amplifier 45 from producing an output signal.

What is claimed is:

1. An electric surgical knife device comprising:
    current generating means for generating an incision current, coagulation current and blend current;
    current selection means for selecting one of the currents generated by said current generating means;
    detector means coupled to said current selection means for generating an output signal when said current selection means selects any two of the currents generated by said current generating means; and
    stop means coupled to said detector means for stopping the current generation by said current generating means in response to the output signal from said detector means.

2. An electric surgical knife device according to claim 1, wherein said current generating means comprises signal generating circuits for generating respectively an incision signal, coagulation signal and blend signal; said signal generating circuits being actuated in response to the selection operation of said current selection means; an attenuator connected to the outputs of the signal generating circuits; an amplifier connected to the output of the attenuator; and an output transformer connected to the output of the amplifier.

3. An electric surgical knife device according to claim 1 or 2, wherein said current selection means comprises a plurality of selection switches; and means for generating a selection signal when one of the selection switches is actuated.

4. An electric surgical knife device according to claim 1 or 2, wherein said stop means is connected between said current selection means and said current generating means, and comprises means for causing, in response to an output signal from said detector means, said current generating means to stop generating a current.

5. An electric surgical knife device according to claim 2, wherein said stop means is coupled to the amplifier of said current generating means, and comprises means for causing, in response to an output signal from said detector means, the amplifier of said current generating means to stop producing an output signal.

* * * * *